Figure 1:
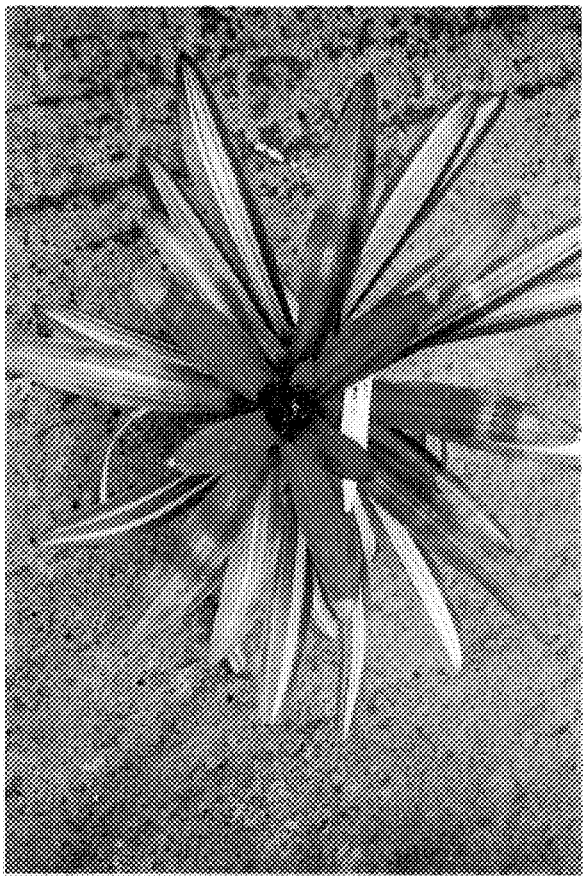

US00PP10717P

United States Patent [19]

Skotak, Jr.

[11] Patent Number: Plant 10,717

[45] Date of Patent: Dec. 8, 1998

[54] NEOREGELIA PLANT NAMED 'MARTIN'

[76] Inventor: Chester Skotak, Jr., Apt 652, Alajuela, Costa Rica

[21] Appl. No.: 893,783

[22] Filed: Jul. 11, 1997

[51] Int. Cl.[6] ..... A01H 5/00

[52] U.S. Cl. ..... Plt./88.8

[58] Field of Search ..... Plt./88.8

[56] References Cited

U.S. PATENT DOCUMENTS

| | | | |
|---|---|---|---|
| P.P. 3,971 | 11/1976 | De Coster | Plt./88.8 |
| P.P. 7,713 | 11/1991 | Kuipers | Plt./88.8 |
| P.P. 9,597 | 7/1996 | Skotak, Jr. | Plt./88.8 |
| P.P. 9,604 | 7/1996 | Skotak, Jr. | Plt./88.8 |
| P.P. 9,627 | 8/1996 | Devroe | Plt./88.8 |

*Primary Examiner*—Howard J. Locker
*Assistant Examiner*—Kent L. Bell
*Attorney, Agent, or Firm*—Foley & Lardner

[57] ABSTRACT

A new and distinct cultivar of Neoregelia plant named 'Martin', characterized by its leaves with a greenish-white (R.H.S. 150C-D) and red-purple (R.H.S. 58A) center with white spotted marmoration on the upper surface of the leaves above the sheath and greyed-purple (R.H.S. 187A) on the surface leaf at the sheath bordered by variegation down the entire length of the leaf and light green margin (R.H.S. 143B-C); the innermost leaves at the center of the rosette, when in flower, are overlayed with red (R.H.S. 53A); the margins of the leaves are finely serrated; and the form of the plant is a uniform rosette with long, lingulate and recurved leaves.

1 Drawing Sheet

The present invention comprises a new and distinctive cultivar of Neoregelia hybrid, botanically known as Neoregelia and hereinafter referred to by the name 'Martin'.

Neoregelia species are tank epiphytes with stemless inflorescences and flowers that barely rise above the water in the center of the plants. 'Martin' can be advantageously grown as a single pot plant in order to display its symmetrically rosette plant form.

The new cultivar is a product of a planned breeding program, and was originated from a cross made by the inventor Chester Skotak, Jr. during such program in Balsa, Costa Rica in 1988. The female or seed parent was an unnamed plant of *Neoregelia carolinae lineata*×*Neoregelia concentrica*. The male or pollen parent was an unnamed plant of *Neoregelia mcWilliamsii L.B.*

'Martin' was discovered and selected as a flowering plant within the progeny of the stated cross by Chester Skotak, Jr. in 1991 in a controlled environment in a nursery in Balsa, Costa Rica.

Subsequent asexual reproduction by removal of offsets has demonstrated that the combination of characteristics as herein disclosed for the new cultivar are firmly fixed and are retained through successive generations of asexual reproduction.

The new cultivar has not been observed under all possible environmental conditions. The phenotype may vary with variations in environment such as temperature, light intensity, and day length, without, however, any variation in the genotype of the plant.

The following traits have been repeatedly observed and are determined to be basic characteristics of 'Martin' which in combination distinguish this Neoregelia as a new and distinct cultivar:

1. Leaves have a greenish-white (R.H.S. 150C-D) and red-purple (R.H.S. 58A) center with white spotted marmoration on the upper surface of the leaves above the sheath and greyed-purple (R.H.S. 187A) on the surface leaf at the sheath bordered by variegation down the entire length of the leaf and light green margin (R.H.S. 143B-C).

2. The innermost leaves at the center of the rosette, when in flower, are overlayed with red (R.H.S. 53A).

3. The margins of the leaves are finely serrated.

4. The form of the plant is a uniform rosette with long, lingulate and recurved leaves.

The new variety Neoregelia 'Martin' can be compared to plants of the species *Neoregelia mcWilliamsii L.B.* and *Neoregelia ultima*. *Neoregelia mcWilliamsii L.B.* does not have finely serrated leaf margins nor variegation, *Neoregelia ultima* does not have upper surface of the leaves above the sheath diffused with red-purple (R.H.S. 58A) nor does *Neoregelia ultima* have a white spotted marmoration on the upper surface of the leaves as does the new cultivar Neoregelia 'Martin'.

In the photographic drawing, FIGURE 1 comprises a top view of a typical plant of the new cultivar.

The following observations, measurements and values describe plants grown in Balsa, Costa Rica and Apopka, Fla., under greenhouse conditions which closely approximate those generally used in horticultural practice. Color references are made to The Royal Horticultural Society (R.H.S.) Colour Chart, except where general color terms are ordinary significance are used.

Classification:

*Botanical.*—Neoregelia hybrid, cv. 'Martin'.

*Commercial.*—Neoregelia 'Martin'.

Parentage:

*Male parent.*—*Neoregelia mcWilliamsii L.B.*

*Female parent.*—*Neoregelia carolinae lineata*× *Neoregelia concentrica.*

Propagation: Vegetative by removal of offsets.

Plant Description:

*Form.*—From 30 to 35 cm tall when grown in 12.5 cm pots and approximately 50 cm or more in overall diameter when fully grown.

*Growth habit.*—Spreading rosette.

Leaves:

*Shape.*—Blades lingulate, recurved, and apiculate.

*Size*—Length about 35–40 cm; width is 1 cm at tip and approximately 3 cm at middle.

*Margin.*—Finely serrated.

*Surface texture.*—Smooth upper and lower surface and finely serrated leaf margin.

*Veins or ribs.*—None.

*Color* (*R.H.S.*).—Upper surface: Greenish-white (150C-D) and red-purple center (58A), which holds its color for approximately 3 to 5 months, with white spotted marmoration on the upper surface of the leaves above the sheath and greyed purple (187A) on the surface leaf at the sheath bordered by variegation down the entire length of the leaf and light green margin (143B-C).

*Lower surface.*—Smooth.

*Number of leaves.*—Average 15–20.

Rosette:

*Leaves forming the socket.*—The socket is about 3.5 cm in overall diameter.

*Color.*—The leaves are overlayed with red 58A.

*Flowers.*—Arrangement: Inflorescence is deeply sunken rosette, simple and many flowered. Color: Petal apex violet-blue 92A with white base. Fruit: White, ovary slenderly ellipsoid and approximately 17 mm long. Duration of the flowers: Individual flowers last one day but flowering is continuous for 5 to 6 weeks.

Reproductive organs:

*Stamens.*—Pale yellow.

*Pistils.*—White; ovary is slenderly ellipsoid and approximately 17 mm long and 6 mm in diameter.

Disease resistance: Good resistance to fungi and insects exhibited in Costa Rica.

General observations: 'Martin' produces large numbers of offsets. Individual plants may produce up to 15 offsets per mature plant within a 3 to 10 month period.

I claim:

1. A new and distinct Neoregelia plant named 'Martin', as illustrated and described.

* * * * *